US012691042B2

(12) United States Patent
Cambos et al.

(10) Patent No.: US 12,691,042 B2
(45) Date of Patent: Jul. 28, 2026

(54) COSMETIC COMPOSITION IN THE FORM OF A COMPACT, IMPACT-RESISTANT POWDER

(71) Applicants: SOCIETE D'EXPLOITATION DE PRODUITS POUR LES INDUSTRIES CHIMIQUES SEPPIC, Paris Cedex (FR); STRAND COSMETIC EUROPE, Lentilly (FR)

(72) Inventors: Sophie Cambos, Paris Cedex (FR); Cécile Taillebois, Paris Cedex (FR); Philippe Msika, Paris Cedex (FR); Emmanuelle Couval, Lentilly (FR); Isabelle Verdelet, Lentilly (FR); Christa Risselada, Lentilly (FR); Julia Pasquet, Lentilly (FR)

(73) Assignees: SOCIETE D'EXPLOITATION DE PRODUITS POUR LES INDUSTRIES CHIMIQUES SEPPIC, Paris (FR); STRAND COSMETIC EUROPE, Lentilly (FR)

( * ) Notice: Subject to any disclaimer, the term of this patent is extended or adjusted under 35 U.S.C. 154(b) by 1061 days.

(21) Appl. No.: 17/631,330

(22) PCT Filed: Jul. 21, 2020

(86) PCT No.: PCT/FR2020/051313

§ 371 (c)(1),
(2) Date: Jan. 28, 2022

(87) PCT Pub. No.: WO2021/019151

PCT Pub. Date: Feb. 4, 2021

(65) Prior Publication Data

US 2022/0257475 A1 Aug. 18, 2022

(30) Foreign Application Priority Data

Jul. 31, 2019 (FR) ...................................... 1908744

(51) Int. Cl.

| | |
|---|---|
| ***A61K 8/02*** | (2006.01) |
| ***A61K 8/25*** | (2006.01) |
| ***A61K 8/34*** | (2006.01) |
| ***A61K 8/37*** | (2006.01) |
| ***A61K 8/81*** | (2006.01) |
| ***A61K 8/891*** | (2006.01) |
| ***A61K 8/92*** | (2006.01) |
| ***A61Q 1/02*** | (2006.01) |
| ***A61Q 17/04*** | (2006.01) |

(52) U.S. Cl.

CPC ................ *A61K 8/022* (2013.01); *A61K 8/25* (2013.01); *A61K 8/342* (2013.01); *A61K 8/37* (2013.01); *A61K 8/8147* (2013.01); *A61K 8/8152* (2013.01); *A61K 8/8158* (2013.01); *A61K 8/891* (2013.01); *A61K 8/922* (2013.01); *A61Q 1/02* (2013.01); *A61Q 17/04* (2013.01); *A61K 2800/43* (2013.01)

(58) Field of Classification Search
None
See application file for complete search history.

(56) References Cited

U.S. PATENT DOCUMENTS

| | | | | |
|---|---|---|---|---|
| 2005/0186235 A1 | 8/2005 | Martin et al. | | |
| 2008/0279899 A1* | 11/2008 | Geffroy | A61Q 1/12 | 514/769 |
| 2012/0157552 A1* | 6/2012 | Braun | C08F 220/06 | 524/547 |
| 2012/0172457 A1 | 7/2012 | Braun et al. | | |
| 2016/0167040 A1 | 6/2016 | Braun et al. | | |

FOREIGN PATENT DOCUMENTS

| | | |
|---|---|---|
| EP | 0 171 979 | 2/1986 |
| EP | 0 971 683 | 1/2000 |
| FR | 2 980 108 | 3/2013 |
| JP | 2013504645 A | 2/2013 |
| JP | 2016525606 A | 8/2016 |

(Continued)

OTHER PUBLICATIONS

Office Action, issued in Korean Patent Application No. 10-2022-7002909 dated Mar. 18, 2025.

(Continued)

*Primary Examiner* — Ali Soroush
*Assistant Examiner* — Afua Bamfoaa Boateng
(74) *Attorney, Agent, or Firm* — NIXON & VANDERHYE

(57) ABSTRACT

Pulverulent composition (Ci) in the form of a powder including, for 100% of the weight thereof: i) from 89.5% to 94.65% by weight of at least one filler (AC); ii) from 5% to 10% by weight of at least one coloured pigment (PC); iii) from 0.35% to 0.5% by weight of at least one polymer of crosslinked anionic polyelectrolyte type (P) which includes, for 100 mol %, from 65 mol % to 95 mol % of monomer units derived from partially or totally salified 2-methyl-2-[(1-oxo-2-propenyl)amino]-1-propanesulfonic acid, from 4.8 mol % to 25 mol % of monomer units derived from at least one neutral monomer chosen from the elements of the group constituted by 2-hydroxyethyl acrylate, 2-hydroxyethyl methacrylate, N,N-dialkyl acrylamides in which each of the alkyl groups includes between one and four carbon atoms, and from 0.1 mol % to 5 mol % of monomer units derived from at least one monomer of formula (I).

11 Claims, No Drawings

(56) References Cited

FOREIGN PATENT DOCUMENTS

| | | |
|---|---|---|
| WO | 93/17660 | 9/1993 |
| WO | 98/44902 | 10/1998 |

OTHER PUBLICATIONS

Search Report and Written Opinion of FR Application No. 1908744 dated Jun. 5, 2020, 10 pages.

International Search Report for PCT/FR2020/051313 dated Sep. 23, 2020, 7 pages.

Written Opinion of the ISA for PCT/FR2020/051313 dated Sep. 23, 2020, 7 pages.

* cited by examiner

COSMETIC COMPOSITION IN THE FORM OF A COMPACT, IMPACT-RESISTANT POWDER

CROSS-REFERENCE TO RELATED APPLICATIONS

This application is the U.S. national phase of International Application No. PCT/FR2020/051313 filed Jul. 21, 2020 which designated the U.S. and claims priority to French Patent Application No. 1908744 filed Jul. 31, 2019, the entire contents of each of which are hereby incorporated by reference.

BACKGROUND OF THE INVENTION

Field of the Invention

The present invention relates to a composition comprising at least one filling agent, at least one colored pigment, and at least one polymer of crosslinked anionic polyelectrolyte type, said composition being in pulverulent form at ambient temperature.

The present invention also relates to a cosmetic composition for topical use which is in a compact form comprising said pulverulent composition and at least one binding agent, exhibiting improved resistance to impacts.

The present invention also relates to the use of such compact cosmetic compositions as products for making up human skin, and to a process for making up human skin employing such compact compositions.

Description of the Related Art

Certain cosmetic compositions for topical use intended for making up the skin, such as, for example, foundations for the face, foundation powders for the face, eyeshadows, or blushers, are generally in the form of compact or cast powders.

For the purposes of the present invention, the term “compact powders” is understood to mean compositions consisting mainly of a mixture of powders, comprising at least one filling agent, at least one pigment, at least one polymer of crosslinked anionic polyelectrolyte type, and at least one binding agent. Once formed, this mixture is shaped by compression in a pot.

These compact powders are generally used by taking a small amount and then applying it to the skin using the fingers, or using an applicator such as for example a brush or sponge.

A quality compact powder requires that it be easy to take up, that it be easy to spread, that the resulting spreading be uniform, and that it have a soft feel once spread on the skin. More specifically, a quality compact powder must have a smooth and flat surface and retain its properties over time. It must also have a sufficiently high impact strength so as not to become fragmented and to retain its properties.

To improve the impact strength properties, designers of compact powders intended for making up the skin have developed solutions based on the optimization of specific binding agents.

For instance, the international patent application published under the number WO9/17660A1 describes the use of a mixture of at least one silicone oil, at least one silicone wax, and at least one silicone resin, constituting a fatty binder intended to be mixed with a solid particulate phase in order subsequently to achieve a compact powder. However, the amounts of binding agents to be employed prove to be significant, and the appearance of the surface of the compact powder then becomes greasy and the transfer to the finger or the applicator before application is less efficient.

The European patent application published under the number EP 0 171 979 A2 describes a process for preparing a composition taking the form of a compact, storage-stable, impact-resistant powder characterized by a flat and smooth surface. The process forming the subject matter of European patent application EP 0 717 979 A2 comprises a step of dispersion of the pulverulent phase in an oil-in-water emulsion formed beforehand, then a step of casting of the obtained dispersion into a mold, and then a step of drying by lyophilization of the previously obtained dispersion. However, such a process has the drawback of being difficult to implement on an industrial scale since it involves expensive equipment which consumes a large amount of energy.

The American patent application published under the number US 2005/0186235A1 describes cosmetic compositions taking the form of compact powders and comprising a pulverulent phase, a solid fatty phase, and requiring, for the preparation thereof, the implementation of a step of melting the solid fatty phase (or wax) which proves to be very energy-consuming. The American patent application published under the number US 2016/167040A1 describes a polymer of crosslinked anionic polyelectrolyte type the polymer backbone of which consists of the ammonium salt of 2-methyl-2-[(1-oxo-2-propenyl)amino]-1-propanesulfonate (ATBS), (2-hydroxyethyl) acrylate (HEA), stearyl methacrylate (SMA) and lauryl methacrylate (LAUMA), crosslinked with trimethylolpropane triacrylate (ATBS/HEA/SMA/LAUMA: 88.1/9.9/1.5/0.5; Polyelectrolyte 1). The American patent application published under the number US 2016/167040A1 also describes a cosmetic composition of compact powder (example 52) which comprises 2% by mass of Polyelectrolyte 1.

The French patent application published under the number FR2980108A1 describes make-up compositions in the form of compact, impact-resistant powders, comprising a pulverulent phase and a liquid phase, but devoid of a polymer of crosslinked anionic polyelectrolyte type.

SUMMARY OF THE INVENTION

In an attempt to overcome these drawbacks, the inventors have sought to provide a cosmetic composition taking the form of a compact, impact-resistant powder, characterized by a good transfer quality for promoting take-up and application to the skin, and prepared according to a process that does not require the input of large amounts of energy.

Thus, a subject of the present invention is a pulverulent composition ($C_1$) in the form of a powder comprising, per 100% of its mass:

i) from 84.3% to 95.8% by mass, preferably from 86.9% to 95.2% by mass, and even more preferentially from 89.5% to 94.65% by mass, of at least one filling agent (FA)

ii) from 4% to 15% by mass, preferably from 4.5% to 12.5% by mass, and even more preferentially from 5% to 10% by mass, of at least one colored pigment (CP)

iii) from 0.2% to 0.7% by mass, preferably from 0.3% to 0.6% by mass, and even more preferentially from 0.35% to 0.5% by mass, of at least one polymer of crosslinked anionic polyelectrolyte type (P) derived from the polymerization, in the presence of at least one crosslinking agent, of partially or totally salified 2-methyl-2-[(1-oxo-2-propenyl)amino]-1-propanesulfonic acid with at least one neutral monomer chosen from the elements of the group consisting of 2-hydroxyethyl acrylate, 2-hydroxyethyl methacrylate, N,N-dialkylacrylamides in which each of the alkyl groups comprises between one and four carbon atoms, and at least one monomer of formula (I):

[Chem 1]

(I)

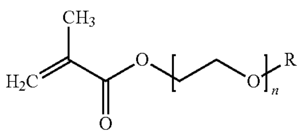

in which R represents a linear or branched alkyl radical comprising from eight to twenty carbon atoms and n represents a number of greater than or equal to zero and less than or equal to twenty.

For the purposes of the present invention, the term "filling agent" is understood to mean a solid chemical substance which is immiscible with water and dispersed in a matrix. A filling agent is introduced into a mixture, in this case a make-up composition, in order to improve its cost as well as certain properties such as for example the covering power on the skin or the density of the pulverulent composition.

According to a more particular aspect, the pulverulent composition (C1) comprises at least 90% by volume of particles with a diameter of less than or equal to 200 micrometers, and more particularly with a diameter of less than or equal to 100 micrometers. In the context of the present invention, this means that the powder composition C1 is comparable to a powder of particles comparable to spheres the diameter of which is less than or equal to 200 micrometers, and more particularly the diameter of which is less than or equal to 100 micrometers. It should be noted that this size of particles makes it possible to achieve a better cohesion of the compact powder subsequently obtained.

This parameter is determined by means of a laser diffraction analyzer, for example the Malvern Mastersizer™ 2000 laser particle sizer, equipped with a dispersing device, for example the dispersing device of MS1-Small Volume Sample Dispersion™ type, and connected to calculation software, which makes it possible to obtain a diffractogram consisting of a superimposition of the diffraction images of each size of particles which are represented in the powder analyzed.

In the analysis of the data thus collected, an initial size distribution is estimated and the theoretical diffractogram is calculated and then compared with the actual data recorded. The differences between the estimated data and the actual data are subsequently minimized using the least squares method. The software subsequently calculates the volume distribution as a fundamental result and any other information is deduced from this result assuming that the particles have a spherical shape.

This method of determination is particularly well suited to the characterization of powders where the particles which constitute them are comparable to spheres with diameters of between 3000 micrometers and 0.1 micrometers, and for dry powders. The use of this type of method has particularly shown good results for particle sizes of greater than 10 micrometers [P. Bowen, "Particle Size Distribution Measurement from Millimeters to Nanometers and from Rods to Platelets"; J. Dispersion Science and Technology, 23(5), pp. 631-662 (2002)]. In the definition of the pulverulent composition ($C_1$), the term "polymer of crosslinked anionic polyelectrolyte type (P)" denotes a non-linear crosslinked anionic polyelectrolyte, which is in the form of a three-dimensional network which is insoluble in water but swellable in water and which thus leads to the production of a chemical gel.

In the definition of the pulverulent composition ($C_1$), the term "partially salified or totally salified" means that the acid function of the 2-methyl-2-[(1-oxo-2-propenyl)amino]-1-propanesulfonic acid is partially or totally salified, generally in the form of an alkali metal salt, for example the sodium salt or the potassium salt, or in the ammonium salt form. In the pulverulent composition ($C_1$) as defined above and which is a subject of the present invention, said polymer of crosslinked anionic polyelectrolyte type (P) employed comprises, per 100 mol %, generally between 65 mol % and 95 mol %, more particularly between 65 mol % and 90 mol %, and even more particularly between 68 mol % and 95 mol %, and even more particularly between 70 mol % and 95 mol %, and even more particularly between 70 mol % and 90 mol %, of monomer units derived from partially or totally salified 2-methyl-2-[(1-oxo-2-propenyl)amino]-1-propanesulfonic acid.

In the pulverulent composition ($C_1$) as defined above and which is a subject of the present invention, said polymer of crosslinked anionic polyelectrolyte type (P) employed comprises, per 100 mol %, generally between 4.8 mol % and 25 mol %, more particularly between 4.8 mol % and 20 mol %, and even more particularly between 5 mol % and 20 mol %, of monomer units of at least one neutral monomer chosen from the elements of the group consisting of 2-hydroxyethyl acrylate, 2-hydroxyethyl methacrylate, N,N-dialkylacrylamides in which each of the alkyl groups comprises between one and four carbon atoms.

According to a particular aspect, in the polymer of crosslinked anionic polyelectrolyte type (P) employed in the pulverulent composition ($C_1$) which is a subject of the present invention, the neutral monomer chosen from N,N-dialkylacrylamides, in which each of the alkyl groups comprises between one and four carbon atoms, is chosen from N,N-dimethylacrylamide, N,N-diethylacrylamide, and N,N-dipropylacrylamide.

In the pulverulent composition ($C_1$) as defined above and which is a subject of the present invention, said polymer of crosslinked anionic polyelectrolyte type (P) employed comprises, per 100 mol %, generally between 0.1 mol % and 10 mol %, more particularly between 0.1 mol % and 5 mol %, and even more particularly between 0.1 mol % and 4.0 mol %, of monomer units of at least one monomer of formula (I).

In formula (I) of the monomer present in said polymer of crosslinked anionic polyelectrolyte type (P) employed in the pulverulent composition ($C_1$) which is a subject of the present invention, "linear or branched alkyl radical comprising from eight to twenty carbon atoms" more particularly denotes for R:

- either a radical derived from linear primary alcohols, for instance the octyl, decyl, undecyl, dodecyl, tridecyl, tetradecyl, pentadecyl, hexadecyl, heptadecyl, octadecyl, nonadecyl or eicosyl radical;
- or a radical derived from Guerbet alcohols, which are branched 1-alkanols corresponding to the general formula:

$$CH_3—(CH_2)_p—CH[CH_3—(CH_2)_{p-2}]—CH_2OH,$$

in which p represents an integer between 2 and 9, for instance 2-ethylhexyl, 2-propylheptyl, 2-butyloctyl, 2-pentylnonyl, 2-hexyldecyl or 2-octyldodecyl radicals;

or a radical derived from isoalkanols corresponding to the general formula:

$$CH_3—CH(CH_3)—(CH_2)_m—CH_2OH,$$

in which m represents an integer between 2 and 16, for instance 4-methylpentyl, 5-methylhexyl, 6-methylheptyl, 15-methylpentadecyl or 16-methylheptadecyl radicals, or 2-hexyloctyl, 2-octyldecyl or 2-hexyldodecyl radicals. According to a particular aspect, a subject of the invention is a pulverulent composition ($C_1$) as described above, characterized in that said polymer of crosslinked anionic polyelectrolyte type (P) comprises, per 100 mol %:

- from 65 mol % to 95 mol %, preferably from 70 mol % to 95 mol %, of monomer units derived from partially or totally salified 2-methyl-2[(1-oxo-2-propenyl) amino]-1-propanesulfonic acid;
- from 4.8 mol % to 25 mol %, preferably from 4.8 mol % to 20 mol %, of monomer units derived from a neutral monomer chosen from the elements of the group consisting of 2-hydroxyethyl acrylate, 2-hydroxyethyl methacrylate, N,N-dialkylacrylamides in which each of the alkyl groups comprises between one and four carbon atoms;
- from 0.1 mol % to 5 mol %, preferably from 0.5 mol % to 5 mol %, and more preferentially from 0.5 mol % to 4 mol %, of monomer units derived from a monomer of formula (I) as defined above,
- from 0.1 mol % to 5 mol %, preferably from 0.5 mol % to 5 mol %, and more preferentially from 0.5 mol % to 3 mol %, of monomer units derived from at least one diethylenic or polyethylenic crosslinking monomer.

According to a particular aspect, a subject of the invention is a pulverulent composition ($C_1$) as described above, characterized in that, in the polymer of crosslinked anionic polyelectrolyte type (P), said neutral monomer is chosen from the elements of the group consisting of 2-hydroxyethyl acrylate or N,N-dimethylacrylamide.

According to a particular aspect, a subject of the invention is a pulverulent composition ($C_1$) as described above, characterized in that, in said polymer of crosslinked anionic polyelectrolyte type (P) and for said monomer of formula (I) as defined above, R represents an alkyl radical comprising from 12 to 18 carbon atoms.

According to another particular aspect, a subject of the invention is a pulverulent composition ($C_1$) as described above, characterized in that, in said polymer of crosslinked anionic polyelectrolyte type (P), R represents an n-dodecyl radical or an isododecyl radical or an n-tetradecyl radical or an n-hexadecyl radical or an n-octadecyl radical and n represents an integer of between 3 and 20.

According to another particular aspect, a subject of the invention is a pulverulent composition ($C_1$) as described above, characterized in that, in said polymer of crosslinked anionic polyelectrolyte type (P), said monomer of formula (I) as defined above is tetraethoxylated lauryl methacrylate of formula ($I_1$), corresponding to formula (I) in which n is equal to four and R represents an n-dodecyl radical.

According to another particular aspect, a subject of the invention is a pulverulent composition ($C_1$) as described above, characterized in that, in said polymer of crosslinked anionic polyelectrolyte type (P), said monomer of formula (I) as defined above is eicosaethoxylated stearyl methacrylate of formula ($I_4$), corresponding to formula (I) in which n is equal to twenty and R represents an n-octadecyl radical.

According to another particular aspect, a subject of the invention is a pulverulent composition ($C_1$) as described above, characterized in that, in said polymer of crosslinked anionic polyelectrolyte type (P), R represents an n-dodecyl radical or an isododecyl radical or an n-tetradecyl radical or an n-hexadecyl radical or an n-octadecyl radical and n is equal to zero. According to another particular aspect, a subject of the invention is a pulverulent composition ($C_1$) as described above, characterized in that, in said polymer of crosslinked anionic polyelectrolyte type (P), said monomer of formula (I) as defined above is lauryl methacrylate of formula ($I_2$), corresponding to formula (I) in which R represents an n-dodecyl radical and/or an isododecyl radical and in which n is equal to zero.

According to another particular aspect, a subject of the invention is a pulverulent composition ($C_1$) as described above, characterized in that, in said polymer of crosslinked anionic polyelectrolyte type (P), said monomer of formula (I) as defined above is stearyl methacrylate of formula ($I_3$), corresponding to formula (I) in which R represents an n-octadecyl radical and in which n is equal to zero.

According to a more particular aspect, a subject of the invention is a pulverulent composition ($C_1$) as described above, characterized in that, in said polymer of crosslinked anionic polyelectrolyte type (P), said monomer of formula (I) is chosen from the elements of the group consisting of tetraethoxylated lauryl methacrylate of formula ($I_1$), corresponding to formula (I) in which R represents an n-dodecyl radical and in which n is equal to four, of lauryl methacrylate of formula ($I_2$), corresponding to formula (I) in which R represents an n-dodecyl radical and in which n is equal to zero, of isodecyl methacrylate of formula ($I'_2$), corresponding to formula (I) in which R represents an isododecyl radical and in which n is equal to zero, and of stearyl methacrylate of formula ($I_3$), corresponding to formula (I) in which R represents an n-octadecyl radical and in which n is equal to zero.

According to a particular aspect, a subject of the invention is a pulverulent composition ($C_1$) as described above, characterized in that, in said polymer of crosslinked anionic polyelectrolyte type (P), said diethylenic or polyethylenic crosslinking monomer is chosen from ethylene glycol dimethacrylate, tetraallyloxyethane, ethylene glycol diacrylate, diallylurea, triallylamine, trimethylolpropane triacrylate, methylenebis(acrylamide), or a mixture of these compounds.

The crosslinked anionic polyelectrolyte (P) employed in the pulverulent composition ($C_1$) as described above may also comprise various additives, such as complexing agents, transfer agents or chain-limiting agents.

The term "transfer agents" or "chain-limiting agents" denotes chemical compounds which, when present during the radical polymerization reaction for preparing the crosslinked anionic polyelectrolyte (P), generate termination reactions, such as disproportionation or recombination reactions, resulting in the formation of polymer chains of shorter length and therefore of lower molecular weight. Mention may be made, as transfer agents or as chain-limiting agents, of thiols such as dodecyl mercaptan, halides such as carbon tetrachloride, short alcohols such as ethanol, n-propanol, isopropanol, n-butanol, or isobutanol, and sodium hypophosphite of chemical formula $NaPO_2H_2$.

According to a particular aspect, a subject of the invention is a pulverulent composition ($C_1$) as described above, characterized in that said polymer of crosslinked anionic polyelectrolyte type (P) is chosen from polymers of 2-methyl-2[(1-oxo-2-propenyl)amino]-1-propanesulfonic acid, partially salified in ammonium form, of N,N-dimethylacrylamide and of tetraethoxylated lauryl methacrylate, crosslinked with trimethylolpropane triacrylate, or from polymers of 2-methyl-2[(1-oxo-2-propenyl)amino]-1-propanesulfonic acid, partially salified in ammonium salt form, of N,N-dimethylacrylamide and of eicosaethoxylated stearyl methacrylate, crosslinked with trimethylolpropane triacrylate.

According to an even more particular aspect, a subject of the invention is a pulverulent composition ($C_1$) as described above, characterized in that said polymer of crosslinked anionic polyelectrolyte type (P) is a polymer of 2-methyl-2[(1-oxo-2-propenyl)amino]-1-propanesulfonic acid, partially or totally salified in ammonium salt form, of N,N-dimethylacrylamide and of tetraethoxylated lauryl methacrylate of formula ($I_1$), crosslinked with trimethylolpropane triacrylate.

According to an even more particular aspect, a subject of the invention is a pulverulent composition ($C_1$) as described above, characterized in that said polymer of crosslinked anionic polyelectrolyte type (P) comprises, per 100 mol %:

- from 65 mol % to 95 mol % of monomer units derived from 2-methyl-2[(1-oxo-2-propenyl)amino]-1-propanesulfonic acid, salified in ammonium form;
- from 4.8 mol % to 25 mol % of monomer units derived from N,N-dimethylacrylamide,
- from 0.1 mol % to 5 mol % of monomer units derived from tetraethoxylated lauryl methacrylate of formula ($I_1$),
- from 0.1 mol % to 5 mol % of monomer units derived from trimethylolpropane triacrylate.

According to an even more particular aspect, a subject of the invention is a pulverulent composition ($C_1$) as described above, characterized in that said polymer of crosslinked anionic polyelectrolyte type (P) is a polymer of 2-methyl-2[(1-oxo-2-propenyl)amino]-1-propanesulfonic acid, partially or totally salified in sodium salt form, of 2-hydroxyethyl acrylate, of lauryl methacrylate of formula ($I_2$) or isodecyl methacrylate of formula ($I'_2$) and of stearyl methacrylate of formula ($I_3$), in a molar ratio of ($I_2$)/($I_3$) or ($I'_2$)/($I_3$) of greater than or equal to 1/10 and less than or equal to 10/1, and crosslinked with trimethylolpropane triacrylate.

According to an even more particular aspect, a subject of the invention is a pulverulent composition ($C_1$) as described above, characterized in that said polymer of crosslinked anionic polyelectrolyte type (P) comprises, per 100 mol %:

- from 70 mol % to 95 mol % of monomer units derived from 2-methyl-2[(1-oxo-2-propenyl)amino]-1-propanesulfonic acid, salified in sodium form;
- from 4.8 mol % to 20 mol % of monomer units derived from 2-hydroxyethyl acrylate,
- from 0.1 mol % to 5 mol % of monomer units derived from lauryl methacrylate of formula ($I_2$) or isodecyl methacrylate of formula ($I'_2$), and from stearyl methacrylate of formula ($I_3$), in a molar ratio of ($I_2$)/($I_3$) or ($I'_2$)/($I_3$) of greater than or equal to 1/6 and less than or equal to 6/1,
- from 0.1 mol % to 5 mol % of trimethylolpropane triacrylate.

The polymer of crosslinked anionic polyelectrolyte type (P) can be obtained by implementing a process comprising:

- a step a) during which all the monomers, an ammonia-containing neutralizing agent for the 2-methyl-2[(1-oxo-2-propenyl)amino]-1-propanesulfonic acid, the crosslinking agent and, if necessary or if desired, the other additives are mixed in an organic solvent, preferably tert-butanol;
- a step b) during which the polymerization reaction is initiated by introducing a free-radical initiator into the dispersion prepared in step a), and then is left to proceed until it is complete;
- optionally a step c) of exchanging the ammonium ion present with a sodium ion or potassium ion;
- a step d) of precipitating the polymer formed on conclusion of step b), optionally of step c);
- optionally a step e) of drying the precipitate obtained on conclusion of step d).

As ammonia-containing neutralizing agent employed in step a) of the process as defined above, there is, for example, ammonia or else ammonium hydrogen carbonate.

In step b) of the process as defined above, the polymerization reaction is initiated at a temperature generally equal to or greater than 50° C. using a radical initiator which produces radicals by homolysis, such as dilauroyl peroxide, azobis(isobutyronitrile) or azo derivatives. According to another embodiment of the process, as defined above, the polymerization reaction is initiated by a redox pair.

In step c) of the process as defined above, the exchange of the ammonium cation with the sodium cation or with the potassium cation is optionally carried out with sodium tert-butoxide or potassium tert-butoxide.

In step d) of the process as defined above, the precipitation of the crosslinked anionic polyelectrolyte (P) is carried out either by evaporation of the solvent or by filtration of the precipitate.

The crosslinked anionic polyelectrolyte (P) thus obtained is then introduced into a mill, such as for example a knife mill, in the presence of at least one colored pigment, and of at least one filling agent, so as to obtain a mixture of ground powders.

This pulverulent mixture is introduced into a metal pot in the presence of at least one binding agent and then subjected to a step of compacting by means of a machine under suitable pressure.

According to a particular aspect, a subject of the invention is a pulverulent composition ($C_1$) as described above, characterized in that the filling agent (FA) is chosen from the elements of the group consisting of fillers of inorganic lamellar type, fillers of organic lamellar type, fillers of inorganic spherical type and fillers of organic spherical type.

Each type of filler enables particular and different qualities to be imparted to the composition ($C_1$) according to the invention. Thus, for example, fillers of inorganic lamellar type generally provide softness, fillers of inorganic spherical type generally provide good disintegration and organic spherical fillers generally have a structuring role and provide softness.

According to a particular aspect, a subject of the invention is a pulverulent composition ($C_1$) as described above, characterized in that the filling agent (FA) is a filler of inorganic lamellar type selected from the elements of the group consisting of talcs or hydrated magnesium silicates; micas or aluminosilicates, such as for example muscovite, margarite, roscoelite, lepidolite, biotite; clays such as for example sericites; kaolin or aluminum silicate hydrate; and boron nitrides.

According to a particular aspect, a subject of the invention is a pulverulent composition ($C_1$) as described above, characterized in that the filling agent (FA) is a filler of organic lamellar type selected from the elements of the group consisting of tetrafluoroethylene polymer powders and lauroyl lysine.

According to a particular aspect, a subject of the invention is a pulverulent composition ($C_1$) as described above, characterized in that the filling agent (FA) is a filler of inorganic spherical type selected from the elements of the group consisting of zinc oxides, titanium oxides, calcium carbonate, magnesium carbonate, magnesium hydrogen carbonate, nonporous spherical silica, hydroxyapatite, silica microspheres with an open porosity, hollow silica microspheres, glass microcapsules, and ceramic microcapsules.

According to a particular aspect, a subject of the invention is a pulverulent composition ($C_1$) as described above, characterized in that the filling agent (FA) is a filler of organic spherical type selected from the elements of the group consisting of metal soaps derived from organic carboxylic acids having from 8 to 22 carbon atoms, such as, for example, zinc stearate, magnesium stearate, lithium stearate, zinc laurate, magnesium myristate; unexpanded synthetic polymer powders, such as, for example, polyethylene powders, polyester powders, such as, for example, polyethylene isophthalate powders or polyethylene terephthalate powders, polyamide powders; powders of crosslinked or uncrosslinked synthetic polymers, such as, for example, polyacrylic acid powders, polymethacrylic acid powders, powders of polystyrene crosslinked with divinylbenzene, silicone resin powders; corn starch, wheat starch, tapioca starch, or rice starch powders; acrylic polymer microspheres, polymethyl methacrylate microspheres, and styrene-divinylbenzene copolymer microspheres. According to a more particular aspect, a subject of the invention is a pulverulent composition ($C_1$) as described above, characterized in that the filling agent (FA) is chosen from the elements of the group consisting of:

- fillers of inorganic lamellar type selected from the group consisting of talcs or hydrated magnesium silicates; micas or aluminosilicates, such as for example muscovite, margarite, roscoelite, lepidolite, biotite; clays such as for example sericites; kaolin or aluminum silicate hydrate; and boron nitrides,
- fillers of organic lamellar type, such as for example tetrafluoroethylene polymer powders and lauroyl lysine,
- fillers of inorganic spherical type selected from the elements of the group consisting of zinc oxides, titanium oxides, calcium carbonate, magnesium carbonate, magnesium hydrogen carbonate, nonporous spherical silica, hydroxyapatite, silica microspheres with an open porosity, hollow silica microspheres, glass microcapsules, and ceramic microcapsules,
- fillers of organic spherical type selected from the elements of the group consisting of metal soaps derived from organic carboxylic acids having from 8 to 22 carbon atoms, such as, for example, zinc stearate, magnesium stearate, lithium stearate, zinc laurate, magnesium myristate; unexpanded synthetic polymer powders, such as, for example, polyethylene powders, polyester powders, such as, for example, polyethylene isophthalate powders or polyethylene terephthalate powders, polyamide powders; powders of crosslinked or uncrosslinked synthetic polymers, such as, for example, polyacrylic acid powders, polymethacrylic acid powders, powders of polystyrene crosslinked with divinylbenzene, silicone resin powders; corn starch, wheat starch, tapioca starch, or rice starch powders; acrylic polymer microspheres, polymethyl methacrylate microspheres, and styrene-divinylbenzene copolymer microspheres.

According to a particular aspect, a subject of the invention is a pulverulent composition ($C_1$) as described above, characterized in that the colored pigment (CP) is chosen from the elements of the group consisting of inorganic pigments, organic pigments and pearlescent pigments.

According to a particular aspect, a subject of the invention is a pulverulent composition ($C_1$) as described above, characterized in that the colored pigment (CP) is an inorganic pigment chosen from the elements of the group consisting of titanium dioxide (rutile or anatase), optionally surface-treated; black, yellow, red and brown iron oxides; manganese violet; ultramarine blue; optionally hydrated chromium oxide; ferric blue.

According to a particular aspect, a subject of the invention is a pulverulent composition ($C_1$) as described above, characterized in that the colored pigment (CP) is an organic pigment selected from the elements of the group consisting of D&C Red pigment, D&C Orange pigment, D&C Yellow pigment, carbon black, lakes based on cochineal carmine.

According to a particular aspect, a subject of the invention is a pulverulent composition ($C_1$) as described above, characterized in that the colored pigment (CP) is a pearlescent pigment selected from the elements of the group consisting of white pearlescent pigments, such as, for example, titanium oxide-coated mica with iron oxides, titanium oxide-coated mica with ferric blue or chromium oxide, titanium oxide-coated mica with an organic pigment, pigments based on bismuth oxychloride.

According to a more particular aspect, a subject of the invention is a pulverulent composition ($C_1$) as described above, characterized in that the colored pigment (CP) is chosen from the elements of the group consisting of:

- inorganic pigments selected from the elements of the group consisting of titanium dioxide (rutile or anatase), optionally surface-treated; black, yellow, red and brown iron oxides; manganese violet; ultramarine blue; optionally hydrated chromium oxide; ferric blue,
- organic pigments selected from the elements of the group consisting of D&C Red pigment, D&C Orange pigment, D&C Yellow pigment, carbon black, lakes based on cochineal carmine,
- pearlescent pigments selected from the elements of the group consisting of white pearlescent pigments, such as, for example, titanium oxide-coated mica with iron oxides, titanium oxide-coated mica with ferric blue or chromium oxide, titanium oxide-coated mica with an organic pigment, pigments based on bismuth oxychloride.

According to a more particular aspect, a subject of the invention is a pulverulent composition ($C_1$) as described above, characterized in that it comprises, per 100% of its mass, a content by mass of water of less than or equal to 2% by mass, preferably of less than or equal to 1.5% by mass, and even more preferentially of less than or equal to 1% by mass.

According to a second aspect, a subject of the invention is a composition for topical use (F) comprising, per 100% of its mass:

- from 90% to 97% by mass, preferably from 92.5% to 96.5% by mass, and even more preferentially from 94% to 96% by mass, of at least one pulverulent composition ($C_1$) as defined above,
- from 3% to 10% by mass, preferably from 3.5% to 7.5% by mass, and even more particularly from 4% to 6% by mass, of at least one fatty binding agent (BA) liquid at 20° C. The expression "for topical use" used in the definition of the composition (F) means that said composition for topical use is employed by application to the skin of the body and of the face, to the hair, to the scalp or to the mucous membranes, whether this is a direct application in the case of a cosmetic, dermocosmetic, dermopharmaceutical or pharmaceutical formulation or an indirect application, for example in the case of a body hygiene product in the form of a textile or paper wipe, or sanitary products intended to be in contact with the skin or the mucous membranes.

In the context of the present invention, the term "fatty binding agent" denotes a fatty, lipophilic chemical composition or substance the function of which is to agglomerate particles in the form of powder or granules into a solid mass so as to reduce the risks of fragmentation thereof under the effect of impacts and to ensure easy take-up thereof.

According to a particular aspect, a subject of the invention is a composition for topical use (F) as described above, characterized in that the fatty binding agent (BA) is selected from the elements of the group consisting of:

i) compositions comprising at least one silicone oil, at least one silicone wax and at least one silicone resin, and optionally at least one silicone gum and at least one phenyl dimethicone, as defined in the international patent application published under the number WO 93/17660 A1, ii) branched alkanes liquid at 20° C., such as for example isododecane or 2,2,4,6,6-pentamethylheptane (CAS number: 31807-55-3/93685-81-5/13475-82-6), isohexadecane CAS=(93685-80-4) or 2,2,4,4,6,8,8-heptamethylnonane (CAS=4390-04-9), iii) mineral oils liquid at 20° C. and at atmospheric pressure, such as for example liquid paraffin, unbranched alkanes such as for example n-decane, n-undecane, n-dodecane, n-tridecane, n-tetradecane, n-pentadecane, n-hexadecane, n-heptadecane, iv) oils of plant origin based on monoglycerides and/or diglycerides and/or triglycerides, denoting chemical substances comprising monoglycerides of formula ($A_1$) and/or of formula ($A'_1$), and/or diglycerides of formula ($A_2$) and/or of formula ($A'_2$), and/or triglycerides of formula ($A_3$) for which the raw materials required for their preparation are plants:

$$CH_3—(CH_2)_{x1}—C(O)—O—CH_2—CH(OH)—CH_2—OH \quad (A_1)$$

$$HO—CH_2—CH[O—C(O)—(CH_2)_{x2}—CH_3]—CH_2—O—H \quad (A'_1)$$

$$CH_3—(CH_2)_{x3}—C(O)—O—CH_2—CH(OH)—CH_2—O—C(O)—(CH_2)_{x4}—CH_3 \quad (A_2)$$

$$CH_3—(CH_2)_{x5}—C(O)—O—CH_2—CH[O—C(O)—(CH_2)_{x6}—CH_3]—CH_2—O—H \quad (A'_2)$$

$$CH_3—(CH_2)_{x7}—C(O)—O—CH_2—CH[O—C(O)—(CH_2)_{x8}—CH_3]—CH_2—O—C(O)—(CH_2)_{x9}—CH_3 \quad (A_3)$$

where x1, x2, x3, x4, x5, x6, x7, x8 and x9, which may be identical or different, represent an integer between 7 and 23.

Among the oils of plant origin based on monoglycerides and/or on diglycerides and/or on triglycerides as defined above, mention may be made, for example, of sweet almond oil, coconut kernel oil, castor oil, olive oil, rapeseed oil, peanut oil, sunflower oil, wheat germ oil, corn germ oil, soybean oil, cottonseed oil, alfalfa oil, poppy seed oil, pumpkin seed oil, woad oil, borage oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil, hemp oil, oils derived from flowers, oils derived from vegetables, triglycerides obtained by esterification reaction between a fatty acid of plant origin and glycerol such as for example glyceryl triisostearate, the caprylic/capric triglyceride sold under the name DUB MCT by Stéarinerie Dubois, the triglycerides obtained by esterification reaction between fatty acids comprising seven carbon atoms and glycerol sold under the name DUB THG by Stéarinerie Dubois, the triglycerides obtained by esterification reaction between fatty acids comprising 22 carbon atoms and glycerol sold under the name Syncrowax HRC by Croda.

v) fatty esters liquid at 20° C. such as for example isostearyl neopentanoate, dicaprylyl caprate, isocetyl stearate, isopropyl myristate, hexadecyl adipate, vi) isoalkanols of formula (II):

$$(CH_3)(CH_3)CH—(CH_2)_r—CH_2—OH, \quad (II)$$

in which formula (II) r represents an integer between 8 and 20, for example the isodecyl, isoundecyl, isododecyl, isotridecyl, isotetradecyl, isopentadecyl, isohexadecyl, isopentadecyl, isooctadecyl, isononadecyl, isoeicosyl or isodocosyl radicals;

vii) Guerbet alcohols of formula (III):

$$CH(C_sH_{2s+1})(C_tH_{2t+1})—CH_2—OH \quad (III)$$

in which formula (III) t is an integer between 6 and 18, s is an integer between 4 and 18 and the sum s+t is greater than or equal to 10 and less than or equal to 22, for example 2-butyloctyl, 2-butyldecyl, 2-hexyloctyl, 2-hexyldecyl, 2-octyldecyl, 2-hexyldodecyl, 2-octyldodecyl, 2-decyltetradecyl, 2-dodecylhexadecyl or 2-tetradecyloctadecyl radicals, viii) fatty alcohols liquid at 20° C. such as for example oleyl alcohol or (Z)-octadec-9-en-1-ol, linoleyl alcohol or cis,cis-9,12-octadecadien-1-ol, linolenyl alcohol or (9Z,12Z,15Z)-9,12,15-octadecatrien-1-ol, ix) silicone derivatives such as, for example, dimethicone, cyclopentasiloxane, vinyl dimethicone, caprylyl methicone, diphenyl dimethicone.

According to a particular aspect, the fatty binding agent (BA) liquid at 20° C. is chosen from the elements of the group consisting of dimethicone, cyclopentasiloxane, vinyl dimethicone, caprylyl methicone, diphenyl dimethicone, isohexadecane, isododecane, liquid paraffin, castor oil, sweet almond oil, macadamia oil, capric/caprylic triglyceride, dicaprylyl caprate, isostearyl neopentanoate, octyldodecanol, hexyldecanol.

According to a more particular aspect, the fatty binding agent is chosen from the elements of the group consisting of castor oil, octyldodecanol, dimethicone, cetearyl ethylhexanoate, and isopropyl myristate.

The composition for topical use (F) which is a subject of the present invention is in particular in the form of blushers, eyeshadows, powders for making up the face, (scented and/or deodorizing) body powders, including powders for the feet and for the hands.

The composition for topical use (F) which is in the form of a compact powder and which is a subject of the present invention may comprise additives customarily employed in the field of, in particular cosmetic, dermocosmetic, pharmaceutical or dermopharmaceutical, formulations for topical use, and chosen from antiseptics, astringents, sunscreens, healing agents, free-radical scavengers, vitamins; demulcents, emollients, moisturizers (glycerol, sorbitol, etc.), skin-lightening agents, fragrances, consistency agents.

Mention may be made, as examples of deodorants optionally present in the composition for topical use (F) which is a subject of the present invention, of alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glyceryl caprate, glyceryl caprylate or polyglyceryl caprate; 1,2-decanediol, 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, or complexes of aluminum chlorohydrate and of glycol, such as the complex of aluminum chlorohydrate and propylene glycol, the complex of aluminum dichlorohydrate and propylene glycol, the complex of aluminum sesquichlorohydrate and propylene glycol, the complex of aluminum chlorohydrate and polyethylene glycol, the complex of aluminum dichlorohydrate and polyethylene glycol or the complex of aluminum sesquichlorohydrate and polyethylene glycol.

Among the agents for protecting against the ultraviolet rays of the sun that may be included in the composition for topical use (F) which is a subject of the present invention, mention may be made of pigments, organic sunscreens and inorganic sunscreens.

As pigments used as agents for protecting against the ultraviolet rays of the sun that may be included in the composition for topical use (F) which is a subject of the present invention, there are, for example, titanium dioxide, brown iron oxides, yellow iron oxides, black iron oxides or red iron oxides, or else white or colored pearlescent pigments such as titanium oxide-coated micas.

As organic sunscreens used as agents for protecting against the ultraviolet rays of the sun that may be included in the composition for topical use (F) which is a subject of the present invention, there are, for example:

- those of the family of benzoic acid derivatives, such as para-aminobenzoic acids (PABAs), notably monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA, butyl esters of N,N-dimethyl PABA;
- those of the family of anthranilic acid derivatives, such as homomenthyl-N-acetyl anthranilate;
- those of the family of salicylic acid derivatives, such as amyl salicylate, homomenthyl salicylate, ethylhexyl salicylate, phenyl salicylate, benzyl salicylate, p-isopropanolphenyl salicylate;
- those of the family of cinnamic acid derivatives, such as ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate or mono(2-ethylhexanoyl)glyceryl di(para-methoxycinnamate);
- those of the family of the benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2-carboxylate, 2-hydroxy-4-(n-octyloxy)benzophenone, 4-hydroxy-3-carboxybenzophenone; 3-(4'-methylbenzylidene)-d,l-camphor, 3-benzylidene-d,l-camphor, camphor benzalkonium methosulfate; urocanic acid, ethyl urocanate;
- those of the family of the derivatives of sulfonic acid, such as 2-phenylbenzimidazole-5-sulfonic acid and its salts; the family of the derivatives of triazine, such as hydroxyphenyltriazine, ethylhexyloxyhydroxyphenyl-4-methoxyphenyltriazine, 2,4,6-trianilino-(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis(2-ethylhexyl) ester of benzoic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole; dibenzazine; dianisoylmethane, 4-methoxy-4"-t-butylbenzoylmethane; 5-(3,3-dimethyl-2-norbornylidene)-3-pentan-2-one; 2-(4-diethylamino-2-hydroxybenzoyl)benzoic acid hexyl ester, 2,4-bis{[4-(2-ethylhexyloxy)-2-hydroxy]phenyl}-6-(4-methoxyphenyl)-1,3,5-triazine, 2,4,6-tris[4-(2-ethylhexyloxycarbonyl)anilino]-1,3,5-triazine, 2-ethylhexyl dimethoxybenzylidene dioxoimidazolidine propionate, the family of diphenylacrylate derivatives, such as 2-ethylhexyl 2-cyano-3,3-diphenyl-2-propenoate or ethyl 2-cyano-3,3-diphenyl-2-propenoate;
- those of the family of the polysiloxanes, such as benzylidene siloxane malonate.

As inorganic sunscreens used as agents for protecting against the ultraviolet rays of the sun that may be included in the composition for topical use (F) which is a subject of the present invention, there are, for example, titanium oxides, zinc oxides, cerium oxide, zirconium oxide, yellow, red or black iron oxides, and chromium oxides. These inorganic screening agents may or may not be micronized, may or may not have undergone surface treatments and may optionally be in the form of aqueous or oily predispersions.

Among the antioxidants that may be included in the composition for topical use (F) which is a subject of the present invention, mention may be made of EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S (INCI name: Tetrasodium Glutamate Diacetate).

Among the active principles that may be included in the composition for topical use (F) which is a subject of the present invention, mention may be made of:

vitamins and their derivatives, in particular their esters, such as retinol (vitamin A) and its esters (retinyl palmitate, for example), ascorbic acid (vitamin C) and its esters, sugar derivatives of ascorbic acid (such as ascorbyl glucoside), tocopherol (vitamin E) and its esters (such as tocopherol acetate), vitamins B3 or B10 (niacinamide and its derivatives); compounds showing a soothing action, in particular Sepicalm™ S, allantoin and bisabolol; anti-inflammatory agents; compounds showing a moisturizing action, such as urea, hydroxyureas, glycerol glucoside, diglycerol glucoside, polyglyceryl glucosides, glycerol, diglycerol or xylityl polyglucoside, sold under the brand name Aquaxyl™; plant extracts rich in polyphenols, such as grape extracts, pine extracts, wine extracts or olive extracts; compounds showing a slimming or lipolytic action, such as caffeine or its derivatives, Adiposlim™, Adipoless™ or fucoxanthin; N-acylated proteins; N-acylated peptides, such as Matrixil™; N-acylated amino acids; partial hydrolyzates of N-acylated proteins; amino acids; peptides; total hydrolyzates of proteins; soybean extracts, for example Raffermine™; wheat extracts, for example Tensine™ or Gliadine™; plant extracts, such as plant extracts rich in tannins, plant extracts rich in isoflavones or plant extracts rich in terpenes; extracts of freshwater or marine algae; extracts of marine plants; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5, Octopirox™ or Sensiva™ SC50; compounds showing an energizing or stimulating property, such as Physiogenyl™, or panthenol and its derivatives, such as Sepicap™ MP; antiaging active principles, such as Sepilift™ DPHP, Lipacide™ PVB, Sepivinol™, Sepivital™, Manoliva™, Phyto-Age™, Timecode™ or Survicode™; antiphotoaging active principles; active principles which protect the integrity of the dermoepidermal junction; active principles which increase the synthesis of the components of the extracellular matrix, such as collagen, elastins or glycosaminoglycans; active principles which act favorably on chemical cell communication, such as cytokines, or physical cell communication, such as integrins; active principles which create a feeling of "heating" on the skin, such as activators of cutaneous microcirculation (such as nicotinic acid derivatives) or products which create a feeling of "coolness" on the skin (such as menthol and derivatives); active principles which improve cutaneous microcirculation, for example venotonics; draining active principles; active principles having a decongestant purpose, such as extracts of ginko *biloba*, ivy, horse chestnut, bamboo, ruscus, butcher's broom, Centalla *asiatica*, fucus, rosemary or willow; agents for tanning or browning the skin, such as, for example, dihydroxyacetone (DHA), erythrulose, mesotartaric aldehyde, glutaraldehyde, glyceraldehyde, alloxan, ninhydrin, plant extracts, such as, for example, extracts of red woods of the genus *Pterocarpus* and of the genus *Baphia*, such as Pteropcarpus *santalinus, Pterocarpus osun, Pterocarpus soyauxii, Pterocarpus erinaceus, Pterocarpus indicus* or *Baphia nitida*, such as those described in the European patent application EP 0 971 683; agents known for their action in facilitating and/or accelerating the tanning and/or browning of human skin, and/or for their action in coloring human skin, such as, for example, carotenoids (and more particularly β-carotene and γ-carotene), the product sold under the brand name "Carrot oil" (INCI name: *Daucus Carota, Helianthus Annuus* Sunflower Oil) by Provital, which contains carotenoids, vitamin E and vitamin K; tyrosine and/or its derivatives, known for their effect on the acceleration of the tanning of human skin in combination with exposure to ultraviolet radiation, such as, for example, the product sold under the brand name "SunTan Accelerator™" by Provital, which contains tyrosine and riboflavins (vitamin B), the complex of tyrosine and of tyrosinase sold under the brand name "Zymo Tan Complex" by Zymo Line, the product sold under the brand name MelanoBronze™ (INCI name: Acetyl Tyrosine, Monk's Pepper Extract (Vitex Agnus-Castus)) by Mibelle which contains acetyl tyrosine, the product sold under the brand name Unipertan VEG-24/242/2002 (INCI name: Butylene Glycol and Acetyl Tyrosine and Hydrolyzed Vegetable Protein and Adenosine Triphosphate) by Unipex, the product sold under the brand name "Try-Excell™" (INCI name: Oleoyl Tyrosine and Luffa *Cylindrica* (Seed) Oil and Oleic Acid) by Sederma which contains extracts of marrow seed (or loofah oil), the product sold under the brand name "Actibronze™" (INCI name: Hydrolyzed Wheat Protein and Acetyl Tyrosine and Copper Gluconate) by Alban Muller, the product sold under the brand name Tyrostan™ (INCI name: Potassium Caproyl Tyrosine) by Synerga, the product sold under the brand name Tyrosinol (INCI name: Sorbitan Isostearate, Glyceryl Oleate, Caproyl Tyrosine) by Synerga, the product sold under the brand name InstaBronze™ (INCI name: Dihydroxyacetone and Acetyl Tyrosine and Copper Gluconate) sold by Alban Muller, the product sold under the brand name Tyrosilane (INCI name: Methylsilanol and Acetyl Tyrosine) by Exsymol; peptides known for their effect in activating melanogenesis, such as, for example, the product sold under the brand name Bronzing SF Peptide Powder (INCI name: Dextran and Octapeptide-5) by Infinitec Activos, the product sold under the brand name Melitane (INCI name: Glycerin and Aqua and Dextran and Acetyl Hexapeptide-1) comprising acetyl hexapeptide-1 known for its alpha-MSH-agonist action, the product sold under the brand name Melatimes Solutions™ (INCI name: Butylene Glycol, Palmitoyl Tripeptide-40) by Lipotec, sugars and sugar derivatives such as, for example, the product sold under the brand name Tanositol™ (INCI name: Inositol) by Provital, the product sold under the brand name Thalitan™ (or Phycosaccharide™ AG) by Codif International (INCI name: Aqua and Hydrolyzed Algin (Laminaria *digitata*) and Magnesium Sulfate and Manganese Sulfate) containing an oligosaccharide of marine origin (guluronic acid and mannuronic acid chelated with magnesium and manganese ions), the product sold under the brand name Melactiva™ (INCI name: Maltodextrin, *Mucuna Pruriens* Seed Extract) by Alban Muller, flavonoid-rich compounds, for instance the product sold under the brand name "Biotanning" (INCI name: Hydrolyzed Citrus Aurantium *Dulcis* Fruit Extract) by Silab and known to be rich in lemon flavonoids (of hesperidins type).

Among the texturing agents that may be included in the composition for topical use (F) which is a subject of the present invention, mention may be made of lauroyl lysine, sold under the name Aminohope™ LL by Ajinomoto, octenyl starch succinate, sold under the name Dryflo™ by National Starch, the myristyl polyglucoside sold by SEPPIC under the name Montanov™ 14, cellulose fibers, cotton fibers or chitosan fibers.

Among the fragrancing or flavoring substances that may be included in the composition for topical use (F) which is a subject of the present invention, mention may be made of:

- extracts of various parts of plants: the flower, leaf, stem or wood, bark or wood moss, fruit or seed, root,
- extracts of flowers such as rose, jasmine, tuberose, champak flower, frangipani flower, ylang-ylang flower, lotus flower, *mimosa* flower, carnation flower, osmanthus flower, acacia flower, sweet orange blossom, bitter orange blossom or neroli, *narcissus* flower, lavender, *gardenia,*
- extracts of leaves, moss, bark, resin or buds such as blackcurrant buds, oakmoss, beech moss, lichen, acacia leaves, basil leaves, valerian leaves, gentian leaves, violet leaves, geranium leaves, labdanum leaves, rosemary, patchouli leaves, *verbena* leaves, cinnamon bark, ash bark, *cassia* bark, cascarilla bark, sandalwood, cedarwood, rosewood, agarwood, birch bark, guaiac wood, balsam of Peru, tolu balsam, benzoin resin, myrrh, labdanum resin, elemi resin, olibanum, opoponax, guggul, needles and branches of pine or spruce or fir,
- extracts of herbs or grasses such as tarragon, lemongrass, sage, thyme,
- fruit or seed extracts such as tonka bean, vanilla pods, cardamom, coriander, star anise, bitter almond, cumin, cloves, juniper berries, citrus fruits such as lemon, orange including sweet lemon and bergamot, mandarin,
- extracts of roots such as the roots of *angelica*, celery, cardamom, iris, sweet-flag, cactus, or vetiver,
- aromatic extracts, absolutes, alcoholates and essential oils.

The term "essential oil" is understood to mean a fragrant product, generally of complex composition, in accordance with cosmetic regulations, obtained from a botanically defined plant raw material. The method for obtaining the essential oil is described in the standard ISO 9235, and these essential oils may possibly have undergone an appropriate subsequent treatment, such as having been deterpenated, desesquiterpenated, or rectified.

As essential oil which can be combined with the composition for topical use (F) which is a subject of the present invention, mention may for example be made of yarrow essential oil, *Acorus calamus* essential oil, garlic essential oil, ajowan essential oil, amyris essential oil, dill essential oil, anise essential oil, *angelica* essential oil, tea tree essential oil, basil essential oil, Bay Saint Thomas essential oil, benzoin essential oil, bergamot essential oil, guaiac wood essential oil, ho wood essential oil, rosewood essential oil, sandalwood essential oil, siam wood essential oil, black birch essential oil, chamomile essential oil, camphor tree essential oil, cinnamon essential oil, cardamom essential oil, carrot essential oil, caraway essential oil, cedar essential oil, celery essential oil, sea fennel essential oil, cistus essential oil, lemon essential oil, citronella essential oil, clementine essential oil, kaffir lime essential oil, copaiba essential oil, coriander essential oil, *cryptomeria* essential oil, cumin essential oil, turmeric essential oil, cypress essential oil, frankincense essential oil, spruce essential oil, tarragon essential oil, fennel essential oil, fragonia essential oil, *galbanum* essential oil, wintergreen essential oil, juniper essential oil, geranium essential oil, ginger essential oil, clove or clove leaf essential oil, helichrysum essential oil, hyssop essential oil, iary essential oil, inula essential oil, katrafay essential oil, khella essential oil, *kunzea* essential oil, lavender essential oil, lavandin essential oil, mandarin essential oil, niaouli essential oil, peppermint essential oil, orange essential oil, grapefruit essential oil, rosemary essential oil, thyme essential oil, ylang ylang essential oil, ravensara essential oil, sage essential oil, cabreuva essential oil, lemongrass essential oil, palmarosa essential oil, St. John's wort essential oil, jasmine essential oil, chamomile essential oil, melissa essential oil, pine essential oil, ginger essential oil, parsley essential oil, *artemisia* essential oil, hemp essential oil, essential oil of hops, or else wild thyme essential oil.

Among the animal "fragrancing or flavoring substances" which can be combined with the composition for topical use (F) which is a subject of the present invention, mention may for example be made of musk, castoreum, civet, ambergris, beeswax absolute and hyraceum.

These substances may also be reconstituted by synthesis.

Among the synthetic "fragrancing or flavoring substances" which can be combined with the composition for topical use (F) which is a subject of the present invention, mention may for example be made of:

a) terpene hydrocarbons (mono- and sesquiterpenes) such as myrcenes (α-myrcene or β-myrcene, and α-myrcene), limonene, α-pinene, β-pinene, camphene, cadinene, cedrene, farnesene, caryophyllene, chamazulene, 1,1-dimethoxy-2,2,5-trimethyl-4-hexene, curcumene, crithmene, himachalenes, limonene, para-cymene, rose oxide, the tetranorlabdane oxide sold under the name Ambrox by Firmenich, terpinenes and terpinolenes, vetivenes, b) esters such as benzyl acetate, bornyl acetate, citronellyl acetate, cedryl acetate, dihydromyrcenyl acetate, dimethylbenzylcarbinyl acetate, ethyl acetate, farnesyl acetate, fenchyl acetate, hexyl acetate, geranyl acetate, isobutyl acetate, isononyl acetate, isopentyl acetate, isobornyl acetate, isopulegyl acetate, linalyl acetate, menthyl acetate, methylphenylcarbinyl acetate, neryl acetate, nonyl acetate, o-t-butylcyclohexyl acetate, phenylethyl acetate, p-tert-butylcyclohexyl acetate, phenylethyl acetate, prenyl acetate, styrallyl acetate, terpenyl acetate, 4-tert-butylcyclohexyl acetate, vetiveryl acetate, methyl anthranilate, benzyl benzoate, isobutyl benzoate, linalyl benzoate, coumarin, ethyl butanoate, benzyl butanoate, isoamyl butanoate, benzyl butyrate, ethyl butyrate, ethyl butyrate, isoamyl butyrate, linalyl butyrate, butyl cinnamate, allyl caproate, ethyl cinnamate, benzyl formate, citronellyl formate, hedione (methyl dihydrojasmonate), geranyl formate, methyl formate, ethylmethylphenyl glycinate, allyl amyl glycolate, allyl heptanoate, phenoxyethyl isobutyrate, cis-3-hexenyl isobutyrate, isoamyl methacrylate, ethyl naphtholate, hexyl neopentanoate, amyl propionate, alkylcyclohexyl propionate, allylcyclohexane propionate, linalyl propionate, styrallyl propionate, citronellyl propionate, methyl salicylate, benzyl salicylate, ethyl salicylate, hexyl tiglate, c) alcohols and phenols such as benzyl alcohol, α-terpineol, anethole, carotol, chavicol, estragole, cineole, cinnamyl alcohol, citronellol, p-cresol, cumyl alcohol, 3,7-dimethyl-1-octanol, dimethylbenzylcarbinol, fenchyl alcohol, eucalyptol, farnesol, eugenol, isononyl alcohol, isoeugenol, guaiacol, geraniol, globulol, linanool, menthol, dihydromyrcenol, nerolidol, nerol, phenylethyl alcohol, safrole, isosafrole, phytol, isophytol, terpineol, tetrahydrolinalool, tetrahydromyrcenol, thymol, vetiverol, undecavertol, d) aldehydes such as phenylacetaldehyde, salicylaldehyde, anisaldehyde, caprylaldehyde, cinnamaldehyde, hexylcinnamaldehyde, bourgeonal, citral (neral), citronellal, hydroxycitronellal, citronellyloxyacetaldehyde, cyclamen aldehyde, cuminaldehyde, cyclal, 2,4-dimethyl-3-cyclohexene-1-carboxaldehyde (ligustral), dodecanal, decylaldehyde, ethanal, octanal, decanal, geranials, helional, lauraldehyde, lactones such as γ-undecalactones, lilial, methyl-n-nonylacetaldehyde, methyloctylacetaldehyde, undecanal, salicylaldehyde, vanillin, e) ketones such as benzylacetone, calone (7-methyl-2H-benzo-1,5-dioxepin-3(4H)-one), carvone, camphor, civetone, damascones, damascenones, ethyl amyl ketone, ethyl hexyl ketone, geranylacetone, jasmone, irones, maltol (3-hydroxy-2-methyl-4H-pyran-4-one), ethyl maltol, menthone, isomenthone, muscone, methylheptenone, ionones such as methylionone, 4-methylacetophenone, methyl pentyl ketone, methyl heptyl ketone, methyl hexyl ketone, α-isomethylionone, and methyl cedryl ketone sold under the name Vertofix by IFF, f) ethers such as anethole, benzyl ethyl ether, cedryl methyl ether, p-cresyl methyl ether, g) artificial musks derived from various nitro compounds, musk ambrettes, musk ketones, musk xylenes, macrocyclic musks, h) nitriles such as trimethyl-3,5,7-octane(ene) nitriles and their α-substituted derivatives, citronellyl nitrile, citronitrile, geranyl nitrile.

According to another aspect, a subject of the invention is the use of a polymer of crosslinked anionic polyelectrolyte type (P) as defined above for improving the impact strength of a cosmetic formulation for topical use (F) as described above.

According to another aspect, a subject of the invention is a process for making up human skin comprising at least one step of applying to said human or animal skin a composition for topical use (F) as defined above.

According to another aspect, a subject of the invention is a composition for topical use (F) according to the invention comprising an effective amount of at least one organic sunscreen and/or at least one inorganic sunscreen, for protecting human skin against the unesthetic effects on said human skin of the ultraviolet rays of the sun.

The term "unesthetic effects on said human skin of the ultraviolet rays of the sun" denotes undesired excessive coloration such as red patches on the skin, a change in the plasticity of the skin which may possibly result in wrinkling of the skin, the appearance of wrinkles and/or pronounced fine lines, in surface desquamation, commonly referred to as "skin peeling", corresponding to the increased detachment of dead skin as a result of prolonged exposure of the skin to ultraviolet rays of the sun.

Said step of applying the composition for topical use (F) to the skin can be carried out using the fingers or an applicator, such as, for example, a brush or a sponge.

The examples that follow illustrate the invention without, however, limiting it.

DESCRIPTION OF THE PREFERRED EMBODIMENTS

Example 1

1.1. Preparation of a terpolymer of ammonium 2-methyl-2-[(1-oxo-2-propenyl)amino]-1-propanesulfonate, N,N-dimethylacrylamide and tetraethoxylated lauryl methacrylate [AMPS/DMAM/LMA (4 EO) 77.4/19.2/3.4 molar], crosslinked with trimethylolpropane triacrylate (TMPTA). [example according to the invention]

592 g of an aqueous solution containing 15% by mass of ammonium 2-methyl-2-[(1-oxo-2-propenyl)amino]-1-propanesulfonate in a tert-butanol/water mixture (97.5/2.5 by volume), 10.1 g of N,N-dimethylacrylamide, 4.2 g of tetraethoxylated lauryl methacrylate and 0.75 g of trimethylolpropane triacrylate are loaded into a reactor maintained at 25° C. with stirring. After a sufficient time to achieve good homogenization of the solution, it is deoxygenated by sparging with nitrogen heated to 70° C. 0.42 g of dilauroyl peroxide is then added and the reaction medium is then maintained for approximately 60 minutes at 70° C. and then for 2 hours at 80° C.

After cooling, the powder which has formed during polymerization is filtered off and dried to obtain the desired product, hereinafter referred to as: Polyelectrolyte 1

1.2 Crosslinked polyelectrolyte of ammonium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.1/9.9/1.0/1.0; Polyelectrolyte 2).

The following are loaded into a reactor maintained at 25° C. with stirring and containing 245 g of tert-butanol:

33.8 g of 2-acrylamido-2-methylpropanesulfonic acid (ATBS);

12.9 g of ammonium hydrogen carbonate;

2.12 g of (2-hydroxyethyl) acrylate (HEA);

0.62 g of stearyl methacrylate (SMA);

0.48 g of lauryl methacrylate (LAUMA);

0.54 g of trimethylolpropane triacrylate (TMPTA).

After a sufficient time to achieve good homogenization of the solution, it is deoxygenated by sparging with nitrogen and then the temperature of the medium is brought to 70° C. When the desired temperature is reached, 0.50 g of dilauroyl peroxide is added. Polymerization starts instantly. The reaction medium is then maintained for approximately 60 minutes at this temperature, and then the mixture is heated to 80° C. This temperature is maintained for 2 hours before cooling. The powder which has formed during polymerization is filtered off and dried to obtain polyelectrolyte 2.

1.3. Preparation of a terpolymer of ammonium 2-methyl-2-[(1-oxo-2-propenyl)amino]-1-propanesulfonate, 2-hydroxyethyl acrylate and tetraethoxylated lauryl methacrylate [AMPS/HEA/LMA (4 EO) 77.4/19.2/3.4 molar], crosslinked with trimethylolpropane triacrylate (TMPTA)

While employing the operating conditions of the process described in example 1.1 above, a reactor, maintained at 25° C. with stirring, is charged with the amount by mass of an aqueous solution containing 15% by mass of ammonium 2-methyl-2-[(1-oxo-2-propenyl)amino]-1-propanesulfonate in a tert-butanol/water mixture (97.5/2.5 by volume) needed to introduce 77.4 molar equivalents of ammonium 2-methyl-2-[(1-oxo-2-propenyl)amino]-1-propanesulfonate, the amount by mass of 2-hydroxyethyl acrylate needed to introduce 19.2 molar equivalents of 2-hydroxyethyl acrylate, the amount by mass of tetraethoxylated lauryl methacrylate needed to introduce 3.4 molar equivalents of tetraethoxylated lauryl methacrylate, and the amount by mass of trimethylolpropane triacrylate needed to obtain the same molar proportion of trimethylolpropane triacrylate as in example 1.1.

After a sufficient time to achieve good homogenization of the solution, it is deoxygenated by sparging with nitrogen heated to 70° C. 0.42 g of dilauroyl peroxide is then added and the reaction medium is then maintained for approximately 60 minutes at 70° C. and then for 2 hours at 80° C.

After cooling, the powder which has formed during polymerization is filtered off and dried to obtain the desired product, hereinafter referred to as: Polyelectrolyte 3.

1.4. Preparation of a copolymer of ammonium 2-methyl-2-[(1-oxo-2-propenyl)amino]-1-propanesulfonate and 2-hydroxyethyl acrylate [AMPS/HEA 90/10 molar], crosslinked with methylenebis(acrylamide) (MBA).

The following are placed a beaker, with stirring:

608.8 grams of a commercial solution containing 50% sodium salt of 2-methyl-2-[(1-oxo-2-propenyl)amino]-1-propanesulfonic acid, 72.6 grams of (2-hydroxyethyl) acrylate, 0.18 grams of sodium diethylenetriaminepentaacetate, and 0.121 grams of methylenebis(acrylamide), the pH of the aqueous phase described above is adjusted to 3.5 by adding 0.7 g of 2-methyl-2-[(1-oxo-2-propenyl)amino]-1-propanesulfonic acid.

In parallel, an organic phase is prepared by successively introducing the following into a stirred beaker:

220 g of Isopar M, 25 g of Montane 70 VG (sorbitan oleate ethoxylated with 20 moles of ethylene oxide, sold by SEPPIC) and 0.2 g of azobis(isobutyronitrile).

The aqueous phase is gradually introduced into the organic phase and then subjected to violent mechanical stirring using an Ultra-Turrax, sold by IKA.

The emulsion obtained is then transferred into a polymerization reactor. The emulsion is subjected to significant sparging with nitrogen so as to remove the oxygen and is cooled to around 5-6° C.

10 grams of a solution containing 1.1% by weight of active material of cumene hydroperoxide in isohexadecane are then introduced. After a sufficient time for good homogenization of the solution, 25 grams of an aqueous solution of sodium metabisulfite (0.2% solution) are introduced in around 25 minutes. During this introduction, the temperature in the polymerization reactor is allowed to rise to the final polymerization temperature and then the reaction medium is maintained at this temperature for approximately 90 minutes.

The resulting mixture is then cooled to a temperature of around 35° C. to obtain an emulsion which is then atomized by means of a Niro™ type device, and Polyelectrolyte 4 is obtained in the form of a powder.

In example 1.4 described above, the monomer of formula (1) was not involved in the polymerization reaction, so as to have a crosslinked anionic polyelectrolyte (Polyelectrolyte 4) intended for comparing the effect associated with the presence of the monomer of formula (1) in the polymer backbone of the crosslinked anionic polyelectrolyte.

Example 2

A—Preparation of Compact Compositions According to the Invention, Comprising Polyelectrolytes 1 to 4, and of Comparative Formulations.

The colored pigments, the filling agent (talc) and the crosslinked anionic polyelectrolyte to be tested are introduced into a Vorwerk brand knife mill, Thermomix TM3300 model. The mixture of powders is then subjected to successive grinding operations, 3 times 30 seconds, at a temperature of 25° C., at a stirring speed of 7700 revolutions/minute. The walls of the bowl are scraped between each grinding operation in order to entrain all the powder during the grinding step.

The binding agent is then distributed over the mixture of powders thus obtained in the bowl of the mill, and this new mixture is then subjected to a grinding operation 3 times for 30 seconds, the walls of the bowl being effectively scraped between each grinding.

An optimum quantity of 11 g of this mixture is introduced into a metal pot 3 centimeters in diameter, and a "Bergamot" type fabric (100% polyamide) is placed on the surface of the pot. This pot is then placed in a manual "compactor", i.e. an apparatus for compacting the powders present in a pot by applying a determined pressure.

A pressure of 130 bar is then applied to the pot for a period of 1 second at a temperature of 25° C.

Formulations (F1), (F2), (F3), (F4) according to the invention and comparative formulations (F5), (F6), (F'1) and (F'2), as described in tables 1 and 2 below, are obtained.

TABLE 1

| | (F1) | (F2) | (F3) | (F'1) | (F'2) |
|---|---|---|---|---|---|
| Polymer (in % by mass) Polyelectrolyte 1 | 0.5% | 0% | 0% | 0% | 0% |
| Polyelectrolyte 2 | 0% | 0.5% | 0% | 0% | 0% |
| Polyelectrolyte 3 | 0% | 0% | 0.5% | 0% | 0% |
| Polyelectrolyte 4 | 0% | 0% | 0% | 0.5% | 0% |
| Filling agent (in % by mass): talc | 88.9% | 88.9% | 88.9% | 88.9% | 89.4% |
| Pigment: Sunpuro TiO2 C47-5001 (INCI = CI 77891) (in % by mass) | 6.1% | 6.1% | 6.1% | 6.1% | 6.1% |
| Fatty binding agent (in % by mass): Eutanol ™G 16 (INCI = hexyldecanol) | 4.5% | 4.5% | 4.5% | 4.5% | 4.5% |

TABLE 2

| | (F4) | (F1) | (F5) | (F6) |
|---|---|---|---|---|
| Polymer (in % by mass) Polyelectrolyte 1 | 0.2% | 0.5% | 1% | 2% |
| Filling agent (in % by mass): talc | 89.2% | 88.9% | 88.4% | 87.4% |
| Colored pigment (in % by mass): Sunpuro TiO2 C47-5001 (INCI = CI 77891) | 6.1% | 6.1% | 6.1% | 6.1% |
| Fatty binding agent (in % by mass): Eutanol ™G 16 (INCI = hexyldecanol) | 4.5% | 4.5% | 4.5% | 4.5% |

B—Demonstration of the Properties and Characteristics of the Compact Formulations According to the Invention Compared to Those of the Prior Art.

Formulations (F1) to (F6) and comparative formulations (F'1) and (F'2) prepared beforehand are then evaluated as follows:

- measurement of their impact strength according to a "drop test" method,
- evaluation of the transfer to the skin at ambient temperature (25° C.),
- evaluation of the transfer to the skin after storage in a humid atmosphere at 50° C.

Experimental protocol for the evaluation of impact strength according to a "drop test" method for formulations (F1) to (F6) and formulations (F'1) and (F'2)

- Principle: determine the number of successive drops starting from which cracks and/or crumbling of the surface of the compact formulation to be tested appear.
- Equipment: metal pot 3 centimeters in diameter containing the compact formulations to be tested, tubular guide for the drop
- Procedure: the formulations to be tested are prepared according to the procedure described above, and are obtained in pots 3 centimeters in diameter. Each pot is placed at a height of 20 centimeters from the ground and is released x times along a tubular guide from said height. After each drop, the experimenter observes the surface of the formulation present in the pot and depending on the case notes "absence of cracks or crumbling on the surface" or "presence of cracks or crumbling on the surface". The experimenter then determines the number of consecutive drops needed for the "presence of cracks or crumbling on the surface" to be observed for the first time. The test is repeated 3 times for each formulation.

Experimental protocol for the evaluation of the quality of the transfer to the skin for formulations (F1) to (F6), and formulation (F'1) at 25° C. and at 50° C.

- Principle: qualify the transfer of the compact formulation to be tested to the experimenter's finger at 25° C. and at 50° C., by estimating the sufficiency of the quantity collected after passing the finger over the pot.
- Equipment: metal pot 3 centimeters in diameter containing the compact formulations to be tested
- Procedure: the formulations to be tested are prepared according to the procedure described above, and are obtained in pots 3 centimeters in diameter. Before each test, the experimenter washes their hands with soap and dries their hands to remove the moisture resulting from rinsing. The experimenter then passes their finger over the surface of a pot comprising the formulation to be tested in order to take some. The experimenter then determines the sufficiency of the quantity collected using the following criteria: "insufficient take-up", "average take-up" and "good take-up".
- Measurement conditions: the formulas are tested after storage for 7 days at 25° C. and at ambient humidity and at 50° C. under humid conditions: for these measurements the pots are placed above a bed of water, in a closed chamber placed in an oven at 50° C. for 7 days. Measurements are taken at 1 day, 3 days, and 7 days.

The results of these evaluations are shown in tables 3 and 4 below.

TABLE 3

| | (F1) | (F2) | (F3) | (F'1) | (F'2) |
|---|---|---|---|---|---|
| Drop test: Number of consecutive drops before cracks appear | 8 | 7 | 5 | 1 | 5 |
| Quality of take-up on the skin at 25° C. Assessment | good take-up | good take-up | good take-up | good take-up | good take-up |
| Quality of take-up on the skin at 50° C. Assessment | good take-up | good take-up | good take-up | good take-up | good take-up |

TABLE 4

| | (F4) | (F1) | (F5) | (F6) |
|---|---|---|---|---|
| Drop test: Number of consecutive drops before cracks appear | 3 | 8 | 7 | 7 |
| Quality of take-up on the skin at 25° C. Assessment | good take-up | good take-up | good take-up | good take-up |
| Quality of take-up on the skin at 50° C. Assessment | good take-up | good take-up | poor take-up | poor take-up |

Comments and Conclusions

The results are considered satisfactory when:

- the number of consecutive drops without the experimenter observing the "presence of cracks or crumbling on the surface", is greater than or equal to 5, and
- the quality of take-up at 25° C. is judged to be "good take-up"
- the quality of take-up at 50° C. is judged to be "good take-up"

Formulations (F1), (F2) and (F3) comprising 0.5% by mass respectively of Polyelectrolyte 1, Polyelectrolyte 2 and Polyelectrolyte 3 show a desired impact strength (number of drops before the observation of cracks respectively of 8, 7 and 5) and a quality of take-up judged to be "good take-up" at 25° C. and 50° C. In contrast, formulation (F'1) comprising a copolymer based on the sodium salt of 2-methyl-2-[(1-oxo-2-propenyl)amino]-1-propanesulfonic acid and 2-hydroxyethyl acrylate, crosslinked with methylenebis (acrylamide), but not comprising a monomer of formula (I) as defined above, exhibits poor impact strength since it only takes a single drop for cracks to appear on the surface of the compact formulation (F'1).

Comparative formulations (F5) and (F6), which comprise a proportion by mass of crosslinked anionic polyelectrolyte (P) of greater than 0.7% in the composition ($C_1$), are characterized by poor take-up on the skin according to the 50° C. test.

The comparative formulation ($F'_2$), which is characterized by the absence of crosslinked anionic polyelectrolyte type polymer (P), shows unimproved impact strength.

The invention claimed is:

1. A pulverulent composition ($C_1$) in the form of a powder comprising, per 100% of its mass:
   i) from 84.3% to 95.8% by mass of at least one filling agent (FA)
   ii) from 4% to 15% by mass of at least one colored pigment (CP)
   iii) from 0.2% to 0.7% by mass of at least one polymer of crosslinked anionic polyelectrolyte type (P) which comprises, per 100 mol %, from 65 mol % to 95 mol % of monomer units derived from partially or totally salified 2-methyl-2-[(1-oxo-2-propenyl)amino]-1-propanesulfonic acid, from 4.8 mol % to 25 mol % of monomer units derived from at least one neutral monomer chosen from the elements of the group consisting of 2-hydroxyethyl acrylate, N,N-dialkylacrylamides in which each of the alkyl groups comprises between one and four carbon atoms, and from 0.1 mol % to 5 mol % of monomer units derived from at least one monomer of formula (I):

(I)

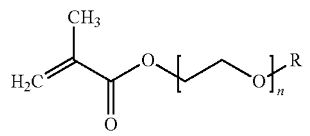

in which R represents a linear or branched alkyl radical comprising from eight to twenty carbon atoms and n represents a number of greater than or equal to zero and of less than or equal to twenty, and from 0.1 mol % to 5 mol % of monomer units derived from at least one diethylenic or polyethylenic crosslinking monomer;

wherein the at least one polymer of crosslinked anionic polyelectrolyte type (P) is (i) a terpolymer of ammonium 2-methyl-2-[(1-oxo-2-propenyl)amino]-1-propanesulfonate, N,N-dimethylacrylamide and tetraethoxylated lauryl methacrylate, crosslinked with trimethylolpropane triacrylate; or (ii) a crosslinked polyelectrolyte of ammonium 2-methyl-2-[(1-oxo-2-propenyl)amino]-1-propanesulfonate, of 2-hydroxyethyl acrylate, of stearyl methacrylate and of lauryl methacrylate, crosslinked with trimethylolpropane triacrylate.

2. The pulverulent composition (C1) as claimed in claim 1, wherein said terpolymer comprises, per 100 mol %:

from 65 mol % to 95 mol % of monomer units derived from 2-methyl-2-[(1-oxo-2-propenyl)amino]-1-propanesulfonic acid, salified in ammonium form;

from 4.8 mol % to 25 mol % of monomer units derived from N,N-dimethylacrylamide, from 0.1 mol % to 5 mol % of monomer units derived from tetraethoxylated lauryl methacrylate of formula ($I_1$), from 0.1 mol % to 5 mol % of monomer units derived from trimethylolpropane triacrylate.

3. The pulverulent composition ($C_1$) as defined in claim 1, wherein said crosslinked polyelectrolyte comprises lauryl methacrylate of formula ($I_2$) and stearyl methacrylate of formula ($I_3$), in a molar ratio of ($I_2$)/($I_3$) of greater than or equal to 1/10 and less than or equal to 10/1.

4. The pulverulent composition ($C_1$) as defined in claim 3, wherein said crosslinked polyelectrolyte comprises, per 100 mol %:

from 70 mol % to 95 mol % of monomer units derived from 2-methyl-2-[(1-oxo-2-propenyl)amino]-1-propanesulfonic acid, salified in sodium form;

from 4.8 mol % to 20 mol % of monomer units derived from 2-hydroxyethyl acrylate, from 0.1 mol % to 5 mol % of monomer units derived from lauryl methacrylate of formula ($I_2$), and from stearyl methacrylate of formula ($I_3$), in a molar ratio of ($I_2$)/($I_3$) of greater than or equal to 1/6 and less than or equal to 6/1, from 0.1 mol % to 5 mol % of trimethylolpropane triacrylate.

5. The pulverulent composition (C1) as defined in claim 1, wherein the filling agent (FA) is chosen from the elements of the group consisting of fillers of inorganic lamellar type, fillers of organic lamellar type, fillers of inorganic spherical type and fillers of organic spherical type.

6. The pulverulent composition ($C_1$) as defined in one or claim 1, wherein the colored pigment (CP) is chosen from the elements of the group consisting of inorganic pigments, organic pigments and pearlescent pigments.

7. The pulverulent composition ($C_1$) as defined in one or claim 1, wherein the composition comprises, per 100% of its mass, a content by mass of water of less than or equal to 2% by mass.

8. A composition suitable for topical use (F) comprising, per 100% of its mass:
   i) from 90% to 97% by mass of at least one pulverulent composition ($C_1$) as defined in claim 1
   ii) from 3% to 10% by mass of at least one fatty binding agent (BA) liquid at 20° C.

9. The composition as defined in claim 8, wherein the binding agent (BA) is selected from the elements of the group consisting of castor oil, octyldodecanol, dimethicone, cetearyl ethylhexanoate, and isopropyl myristate.

10. The composition suitable for topical use (F) as claimed in claim 8, comprising an effective amount of at least one organic sunscreen and/or at least one inorganic sunscreen, for protecting human skin against the unesthetic effects on said human skin of the ultraviolet rays of the sun.

11. A process for making up human skin, wherein the process comprises at least one step of applying to said human skin a composition suitable for topical use (F) as defined in claim 8.

* * * * *